United States Patent [19]

Owens

[11] Patent Number: 5,357,693
[45] Date of Patent: Oct. 25, 1994

[54] FOOTWEAR WITH THERAPEUTIC PAD

[75] Inventor: Byron C. Owens, Asheboro, N.C.

[73] Assignee: Vesture Corporation, Randleman, N.C.

[21] Appl. No.: 144,345

[22] Filed: Nov. 1, 1993

Related U.S. Application Data

[63] Continuation-in-part of Ser. No. 969,959, Dec. 3, 1992, which is a continuation-in-part of Ser. No. 871,826, Apr. 21, 1992, abandoned, which is a continuation of Ser. No. 643,344, Jan. 22, 1991, abandoned, which is a continuation-in-part of Ser. No. 486,806, Feb. 26, 1990, abandoned.

[51] Int. Cl.$^5$ ............................ A43B 7/02; A43B 19/00
[52] U.S. Cl. .................................... 36/71; 36/2.6; 36/45; 36/54; 36/136
[58] Field of Search .............. 36/71, 88, 45, 136, 36/132, 141, 9 R, 89, 93, 2.6, 54, 72 R

[56] References Cited

U.S. PATENT DOCUMENTS

| | | | |
|---|---|---|---|
| 520,417 | 5/1894 | Foss | 36/10 |
| 601,192 | 3/1898 | Woodside | 36/54 |
| 1,215,198 | 2/1917 | Rothstein | 36/71 |
| 1,663,376 | 3/1928 | Koller | 36/9 R |
| 1,753,415 | 4/1930 | Hepburn | 36/54 |
| 2,244,031 | 6/1941 | Teehan | 36/54 |
| 2,675,630 | 4/1954 | Youmans | 36/44 |
| 3,059,352 | 10/1962 | Clason | 36/54 |
| 3,284,931 | 11/1966 | Dassler | 36/54 |
| 3,997,983 | 12/1976 | Terhoeven | 36/72 R |
| 4,023,282 | 5/1977 | Ziegelheafer | 36/2.6 |
| 4,094,080 | 6/1978 | Sanders | 36/2.6 |
| 4,123,855 | 11/1978 | Thedford | 36/29 |
| 4,249,319 | 2/1981 | Yoshida | 36/2.6 |
| 4,373,274 | 2/1983 | Michalski | 36/2.6 |
| 4,644,673 | 2/1987 | Gamm | 36/114 |
| 4,743,726 | 5/1988 | Hughes et al. | 219/10.55 F |
| 4,756,311 | 7/1988 | Francis, Jr. | 128/403 |
| 4,841,646 | 6/1989 | Maurer, Jr. | 36/2.6 |
| 4,849,593 | 7/1989 | Hughes et al. | 219/10.55 R |
| 5,038,779 | 8/1991 | Barry et al. | 128/402 |
| 5,050,598 | 9/1991 | Tucker | 36/2.6 |
| 5,052,369 | 10/1991 | Johnson | 206/545 |

Primary Examiner—Paul T. Sewell
Assistant Examiner—Marie Denise Patterson

[57] ABSTRACT

A therapeutic pad is used in footwear which has a liquid absorbent to prevent liquid leakage in the event the sealed envelope of the pad is ruptured. The footwear includes a pair of compartments which substantially surround the foot cavity for receiving the therapeutic pad.

12 Claims, 11 Drawing Sheets

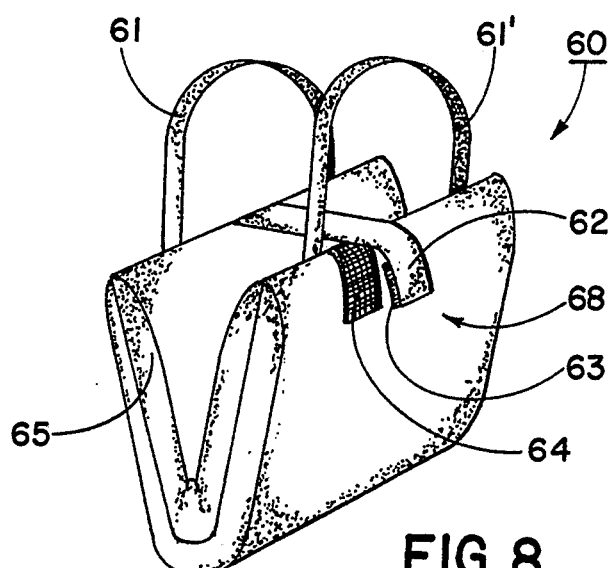
FIG. 8
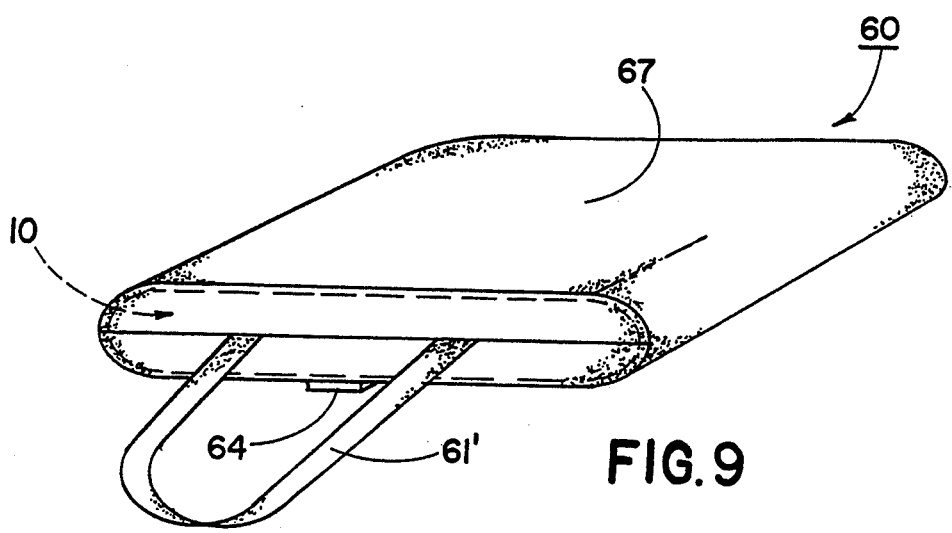
FIG. 9
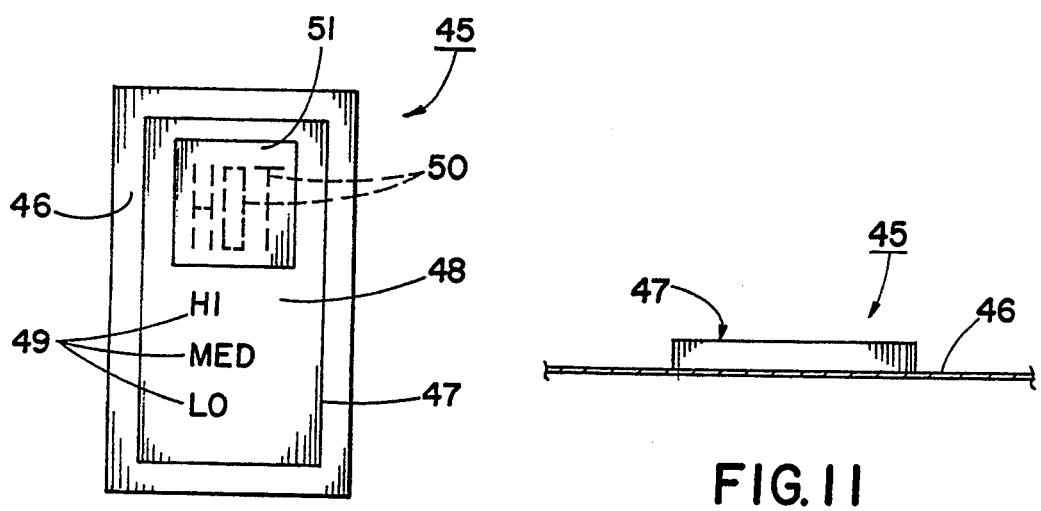
FIG. 10
FIG. 11

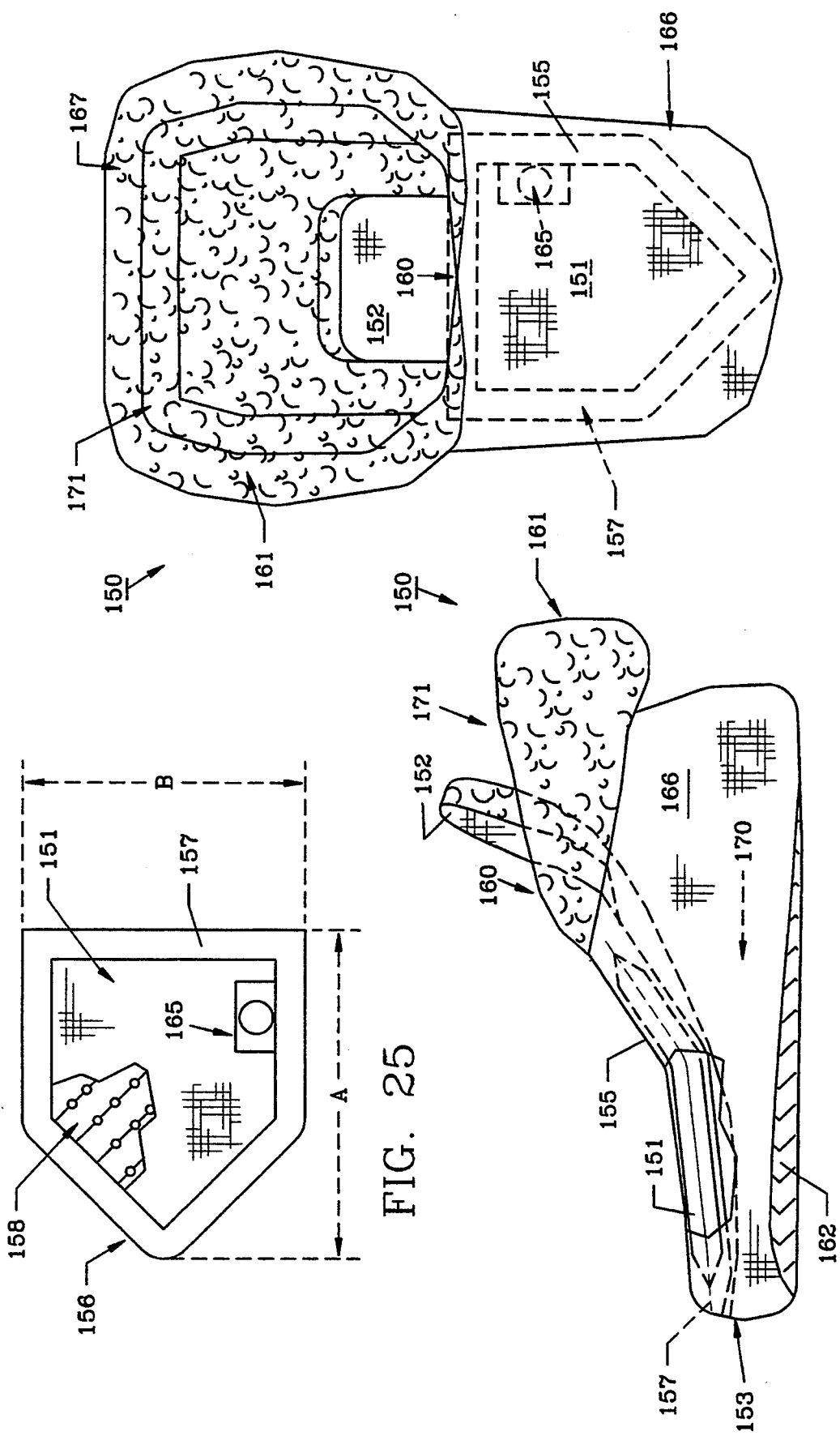

FOOTWEAR WITH THERAPEUTIC PAD

This is a continuation-in-part application of pending patent application Ser. No. 07/969,959 filed 03 Dec. 1992 which in turn was a continuation-in-part of application Ser. No. 07/871,826 filed 21 Apr. 1992 now abandoned which was a continuation of application Ser. No. 07/643,344 filed 22 Jan. 1991, now abandoned which was a continuation-in-part of patent application Ser. No. 07/486,806 filed 26 Feb. 1990, now abandoned.

BACKGROUND OF THE INVENTION

1. Field Of The Invention

The invention relates to footwear using therapeutic pads and specifically to therapeutic pads for applying heat or removing heat from particular body surface areas of the user to soothe muscles and joints.

2. Description Of The Prior Art And Objectives Of The Invention

It is well-known that liquid containing therapeutic pads are designed for heating and cooling applications for parts of the human body such as a bruised arm, thigh or back muscle or to relieve pain from a sprained ankle. Therapeutic heating pads may contain liquids such as in conventional hot water bottles or may be of the more modern style which are sealed liquid pouches that can be microwaved and then applied to sore muscles or joints. It is also well-known that certain therapeutic pads are designed to be cooled or frozen in freezers or the like whereby they can be removed and placed on sprained ankles or otherwise positioned to relieve pain by withdrawing heat from the user's body. It has also been known in the past to provide a comforter in the form of a stuffed or yieldable object such as a stuffed toy animal whereby a hot water bottle can be inserted within the object and the object can then be placed in a child's bed whereby the child can be comforted by the heat emanating therefrom. In recent years therapeutic pads have been manufactured and sold consisting of flexible plastic envelopes in which water type solutions are contained. The pad is placed in a vacuum pump whereby the air within the bag will be withdrawn and the bag can then be heat sealed with the liquid therein. Pads which have been used in the past to contain liquids for either heating or cooling have been susceptible to breakage and rupturing whereby the user's clothes, furniture, bed sheets and the like have become damaged and must be disposed of or at least cleaned. Also, adults are greatly concerned with small children that need to use therapeutic pads which may leak and accordingly this fear has deterred their use to some degree.

Thus, with the known problems and disadvantages associated with prior art therapeutic pads, the present invention was conceived and one if its objectives is to provide a therapeutic pad which is constructed to prevent leaks, even in the event the outer envelope is ruptured.

It is yet another objective of the present invention to provide a therapeutic pad and method for forming the same in which the pad has a liquid absorbent which, in the event of seal breakage the liquid will be absorbed and will substantially remain within the envelope.

It is yet another objective of the present invention to provide a therapeutic pad which is vacuum formed and which contains a liquid and liquid absorbent whereby the liquid absorbent is in a resilient compressed state.

It is yet another objective of the present invention to provide a method for easily forming a therapeutic pad which will aid in preventing injury to clothing, bed sheets or other materials against which it is placed in the event of rupture due in part to an improved moisture impervious covering.

It is also an objective of the present invention to provide a therapeutic pad which includes a readily visible temperature indication device which will provide additional safety and efficiency in heating the pad.

It is still another objective to provide a therapeutic pad which has been shaped to fit within specially designed footwear to provide warmth and comfort to the feet of the wearer.

Various other objectives and advantages of the present invention become apparent to those skilled in the art as a more detailed description of the embodiments is presented below.

SUMMARY OF THE INVENTION

In view of the aforesaid objectives the invention herein provides a new and improved therapeutic pad which solves many problems of conventional pads as are now being used. The pad of the invention is formed from a permanently sealed thin, flexible outer envelope and included therein is a liquid filled absorbent such as a synthetic sponge which is compressed prior to envelope sealing. The compressed sponge retains liquid and in the event the envelope is accidentally punctured, the sponge will rapidly enlarge in size preventing any liquid within the pouch from escaping through the rupture. The method of forming the therapeutic pad consists of placing a liquid containing thermoplastic envelope is a vacuum chamber apparatus. A sponge is inserted into the liquid and thereafter, by the use of a vacuum pump, air is evacuated from the envelope and the sponge is compressed as the envelope deflates. Once a sufficient vacuum is pulled, for example 24 inches of Hg., the envelope is sealed by a pair of heating elements. The sealed envelope is placed in a water impervious envelope having a rubberized covering to increase the safety and durability. A thermochromic liquid crystal temperature indication device is affixed to the outer surface of the rubberized covering to indicate when the interior liquid has reached sufficient temperatures. The therapeutic pad is then ready to be placed in a fabric cover and may be microwaved or otherwise heated prior to use. Somewhat similar steps are used to form a therapeutic pad which can be used by cooling or freezing by placing in a refrigerator or freezer. Therapeutic pads of the invention can be placed within a yieldable object such as a teddy bear, pillow or the like whereby the object can be used for comforting a child at bed time. Also, the therapeutic pad can be placed in footwear which has been designed to receive the same for those that need, for example, heat applied to the feet.

BRIEF DESCRIPTION OF THE DRAWINGS

FIG. 8 depicts a foldable seat cushion as used with the heatable therapeutic pad;

FIG. 9 shows the seat cushion of FIG. 8 in perspective view unfolded;

FIG. 10 pictures an enlarged view of a typical temperature indication device having temperature indicia as used with the invention, in a top-plan view;

FIG. 11 depicts the temperature indication device of FIG. 10 in an end elevational view;

FIG. 23 is a side elevational view of another embodiment of footwear containing a therapeutic pad;

FIG. 24 demonstrates a top plan view of the footwear as shown in FIG. 23; and

FIG. 25 demonstrates a top plan view of the therapeutic pad which is insertable therein.

DESCRIPTION OF THE PREFERRED EMBODIMENTS

Figure 2:
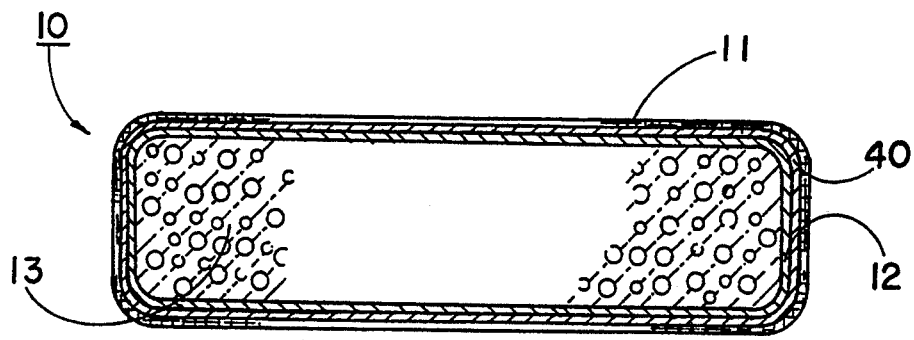
FIG. 2 demonstrates a cross-sectional view of the pad as shown in FIG. 1 along lines 2—2.

The preferred form of the therapeutic pad of the invention is shown in cross-sectional view in FIG. 2 and includes a fabric outer cover, a thermoplastic envelope which contains a liquid filled sponge which has been compressed to approximately forty percent of its original size. The sponge compression provides unique features to the device for use in a variety of applications whereby, in the event of an inadvertent rupture of the envelope, the sponge will expand and absorb any liquid which may otherwise drain through the rupture and contact human skin causing burns or irritations, stain bed sheets, clothing or the like. The preferred method of making forming the therapeutic pad comprises placing a flexible thermoplastic envelope such as may be formed from polyethylene in a conventional vacuum forming and heat sealing cabinet. Liquid is introduced into the envelope and a sponge is also positioned therein. With the vacuuming device turned on, the air is pumped from the envelope and as the envelope collapses, is the sponge compressed. Once a sufficient vacuum has been drawn, such as twenty-four inches of Hg. as demonstrated on a vacuum gauge, the heat sealing elements are activated to permanently seal the envelope where it can then be placed in a rubberized covering and an exterior fabric cover for later microwaving and application to a sore muscle. The therapeutic pad can be used in footwear such as specially deigned shoes or slippers for those that need therapy applied to the feet. The preferred form of footwear includes a slipper type shoe having a rear opening for sliding the heated pad therein.

DETAILED DESCRIPTION OF THE DRAWINGS AND OPERATION OF THE INVENTION

Figure 1:
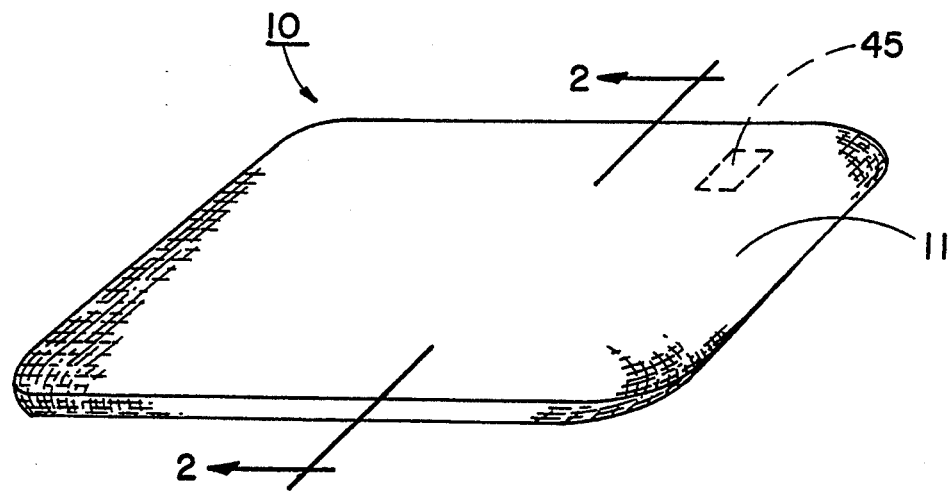
FIG. 1 illustrates a typical pad of the invention as shown herein.

Turning now to the drawings, therapeutic pad 10 as shown in FIG. 1 contains a liquid filled microwavable pad as used for sore muscles by athletes or others. The pad can be placed in a conventional microwave oven and heated for approximately five minutes. The pad is then removed and placed against the sore muscle or joint to provide warm therapeutic relief. Other pads are made which can be placed in the freezer of a home refrigerator and once they have reached the desired temperature, can be used to extract heat from a sore muscle, ankle joint or the like to reduce swelling and inflammation.

Figure 3:
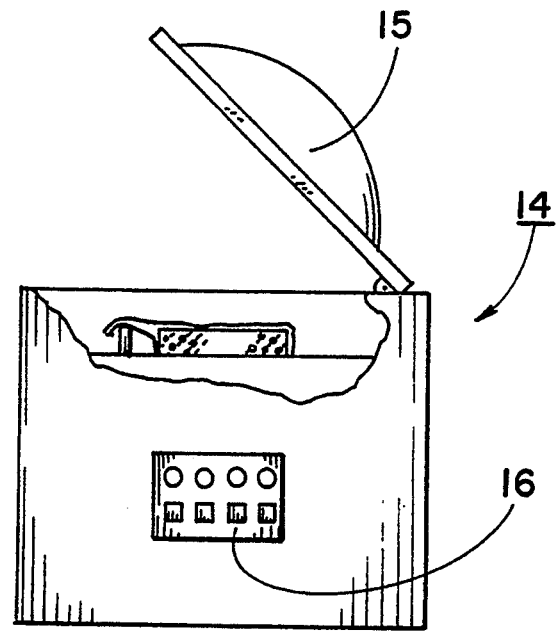
FIG. 3 pictures a conventional combination vacuum forming and heat sealing unit.

Pad 10 is shown in FIG. 2 in cross-sectional view whereby cover 11 is formed from a cotton fabric and encloses sealed flexible plastic envelope 12 which may be for example, formed from polyethylene or other suitable and durable plastics. Means 13 to absorb liquid is positioned within envelope 12 and in a compressed state as will be hereinafter explained. Means 13 consist of a synthetic nylon sponge although other resilient, compressible absorbents may also be used such as natural sponges, or other synthetic or natural structures. As seen in FIG. 2, absorbent means 13 is compressed to approximately forty percent of its normal size and as would be understood, if envelope 12 is ruptured, means 13 would attempt to recover to its normal, non-compressed configuration. A water impervious covering 40 is shown in FIGS. 2 and 3 which may consist of cotton flannel/rubberized sheathing, a neoprene coated nylon sheeting, a natural rubberized sheeting or other similar combinations. These materials are conventional and are commonly used in hospitals and for incontinence uses on beds, chairs and for other articles. Their durability and high resistance to tearing and puncturing make them desirable and they have been found to provide superior water impervious coatings for therapeutic pads.

Figure 5:
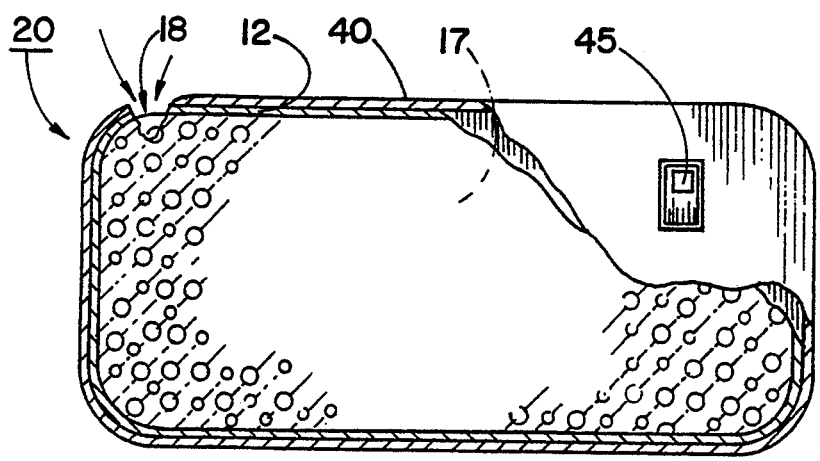
FIG. 5 illustrates the expansion of the liquid absorbent such as if a leak should occur in the envelope.
Figure 4A:
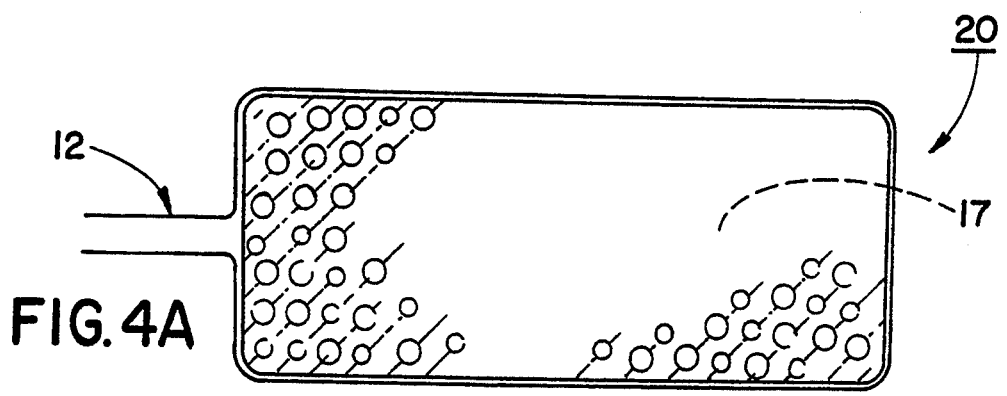
FIG. 4A depicts the envelope of the therapeutic pad having a liquid and absorbent therein prior to vacuuming.
Figure 4B:
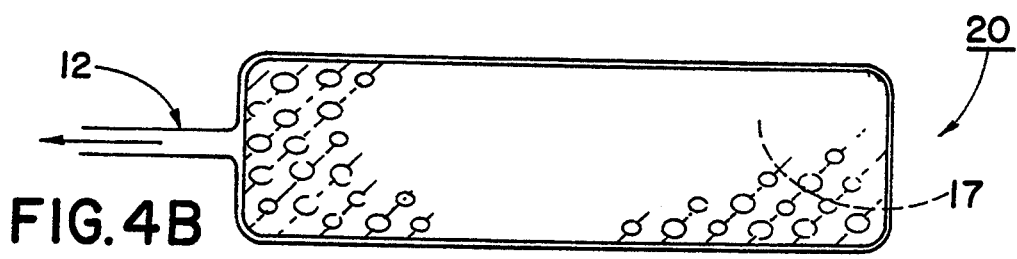
FIG. 4B illustrates the envelope of FIG. 4A but with a partial vacuum applied.
Figure 4C:
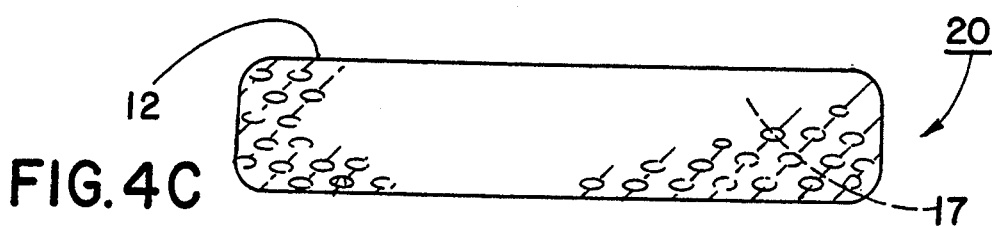
FIG. 4C shows the envelope which has been fully vacuumed and sealed prior to insertion into a rubberized covering.

In FIG. 3, combination vacuum and heat sealing device 14 is shown having a chamber lid 15 and control panel 16 for vacuum forming and heat sealing thermoplastic envelopes such as envelope 12 as shown in FIG. 2. Device 14 is conventional and is sold throughout the food industry for vacuum packaging meats and other products. In forming therapeutic pads as presented herein, an empty envelope 12 is filled with a suitable amount of liquid such as a water solution or proprietary formula and a sponge 17 as shown in FIG. 4A is placed therein. As shown in FIGS. 4B and 4C sponge 17 is reduced in size as air is evacuated from collapsing envelope 12 and as would be understood in FIG. 4C, with sponge 17 substantially compressed once the vacuum pressure reaches the controlled level of for example, 24 inches of Hg., envelope 12 is permanently heat sealed, maintaining sponge 17 in a compressed posture. Thereafter, cover 11 can be applied thereto as desired. In the event the seal of envelope 12 is broken or in the event envelope 12 is ruptured at some surface point, air as depicted by the arrow in FIG. 5 will rush into envelope 12 allowing sponge 17 to expand and close off rupture 18 while absorbing any liquid which may attempt to drain therethrough. Hence, with the rupture so protected and filled with sponge 17, therapeutic pad 20 is safe for use in that it will not substantially cause injury, damage or staining to children, bed linens, clothes or the like. A rubberized impervious covering 40 is shown in FIG. 5 surrounding envelope 12 to provide a more durable product. The aforementioned rubberized covering 40 may be formed from a cotton flannel which is bonded to a natural or synthetic rubber or may consist of nylon sheathing which has been neoprene coated as is well-known in the in the incontinence product art. Also, in FIG. 5 liquid crystal temperature indicator 45 is shown positioned atop pad 20. Liquid crystal temperature indicating devices are old and have been used many years to indicate temperatures and temperature changes. Temperature indicator 45 is affixed by an adhesive or by other means to rubberized covering 40 to assist one in determining the temperature and the time required to bring pad 20 to its desired temperature level in a microwave oven during heating.

As seen in FIGS. 10 and 11, thermochromic liquid crystal temperature indicator 45 consists of a transparent adhesive backed base 46 for attachment to covering 40. Affixed to base 46 is polymer pouch 47 for containing liquid crystals. Various temperature indicia is available and as shown in FIG. 10, pouch 47 includes a black background top surface 48 at room temperature with white letters 49 which indicate high, medium and low temperatures. A red background 51 is shown at the top of pouch 47 with ghost letters 50 which spell "HOT" contained therein. Thus, when room temperature pad 20 is first placed in a microwave oven, letters 49, are white and as the temperature increases the letters of "HI", "MED" and "LO", change color from white to red. Also, background 51 which is red at room temperature turns white upon sufficient heating thereby allowing ghost letters 50 to become very apparent as they turn a solid, dark red color. At this point the pad has reached its desired temperature level and may be removed from the microwave oven for use.

Figure 6:
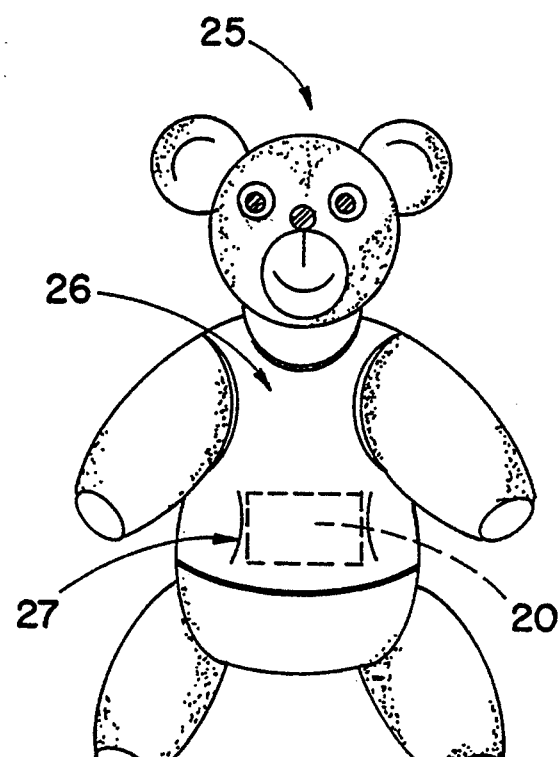
FIG. 6 presents a comforter object in the form of a stuffed teddy bear with a therapeutic pad in the vest worn on the chest of the bear.
Figure 7:
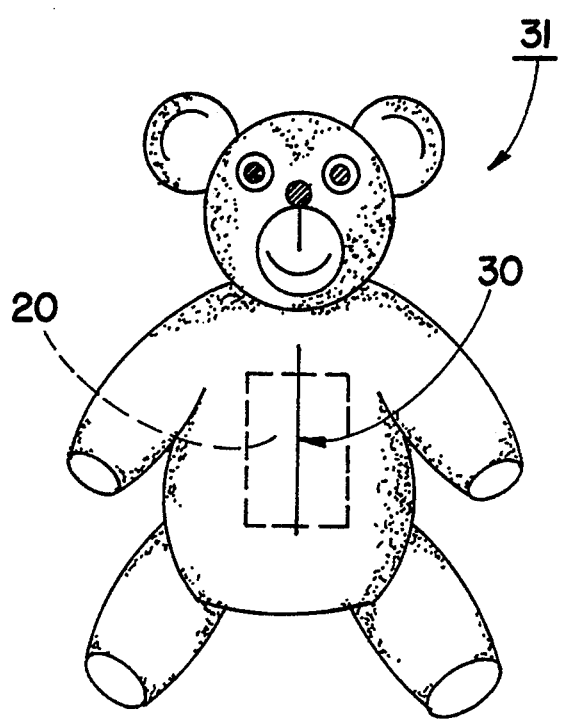
FIG. 7 demonstrates another embodiment of a stuffed object having a therapeutic pad positioned within.

While therapeutic pad 20 as shown in FIGS. 1 and 2 can be applied directly to human skin, it has been determined that children can be relieved of daily emotional distress which accumulates by providing them with a stuffed object such as a toy bear which dispenses heat therefrom. As illustrated in FIG. 6, toy stuffed bear 25 is wearing vest 26 which includes a front pocket 27 for maintaining microwavable therapeutic pad 20. Toy bear 25 can then be placed in a child's crib or bed and pad 20 will provide warmth therefrom for a period of time to soothe and comfort the mind and body of the child. Various other objects such as pillows, or other animal designs could likewise be utilized a vest, gown or some other pad support maintained on the outside of the object. Additionally, as shown in FIG. 7, a stuffed toy animal 31 could be manufactured with an inner pocket 30 into which the therapeutic pad 20, with its means for liquid absorption is located and would be extremely beneficial under conditions of rough handling or the like that may cause envelope 12 as shown in FIG. 2 to rupture since means 13 will prevent drainage into toy bear 31, and thereby preventing damage and inconvenience.

In FIGS. 8 and 9 seat cushion 60 is shown which comprises an outer, durable fabric or other suitable cover 67 having joined thereto handles 61, 61'. Seat cushion 60 can be closed as shown in FIG. 8 and latched with closure strap 62 having distal end hook and loop fastener 63 for engaging hook and loop fastener 64 which is affixed on side 68 of seat cushion 60. Thus, pad 10 can be placed in a microwave oven and heated to the desired temperature level prior to a football game or the like where it is inserted into cover 67, folded, latched with closure strap 62 and carried to a football game such as are played in outside stadiums. Upon arrival at the stadium seat, closure strap 62 is then released allowing seat cushion 62 to open to a flat posture as shown in FIG. 9 where it is placed on the bench seat or the like. The user can then sit on soft cushion 65 as shown in FIG. 9 and remain warm and comfortable through several hours of outside activity. Upon leaving the user can refold seat cushion 60 by reattaching closure strap 62 and then easily transport seat cushion 60 back to his home or other destination.

Figure 12:
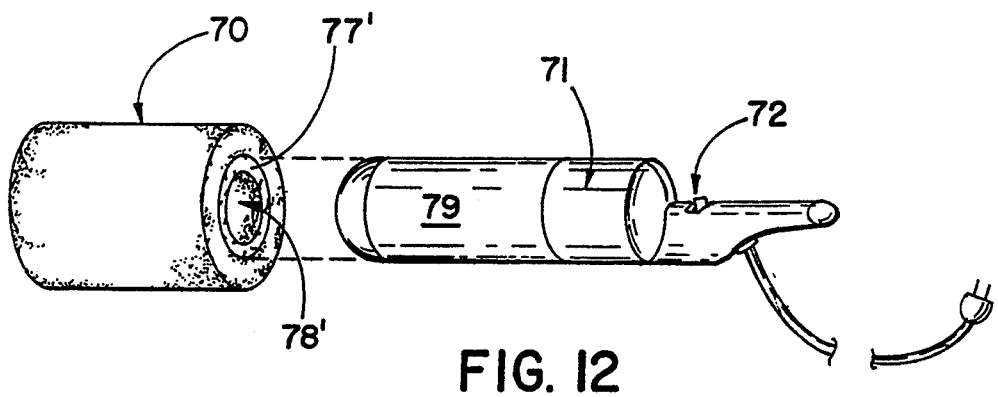
FIG. 12 presents a conventional electric vibrator with cylindrical therapeutic pad removed therefrom.
Figure 13:
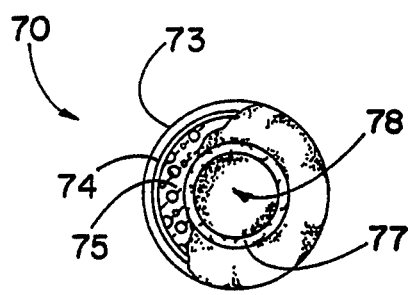
FIG. 13 demonstrates an end view of the cylindrical pad in cut-away fashion.

As shown in FIGS. 12 and 13, cylindrical therapeutic pad 70 is shown which fits over conventional elongated electrical vibrator 71. Vibrator 71 applies a massaging action to sore muscles and with liquid filled cylindrical pad 70 thereon cold or heat therapy can be provided. As seen in the cut-away view of pad 70 in FIG. 13, cylindrical therapeutic pad 70 which may be four inches in diameter and five inches in length includes an outer cloth covering 73, a rubberized inner covering or layer 74, a plastic envelope 75 which contains liquid filled sponge 76 therein. Elastic bands 77, 77' are positioned at each end of the cylindrical member to assist in holding cylindrical pad 70 on vibrator 71 during use. As would be understood, cylindrical pad 70 can be manually slid onto and off vibrator 71 as opening 78 is slightly larger in diameter than vibrator body 79. Elastic bands 77, 77' surround opening 78, 78' and resiliently maintain therapeutic pad 70 on vibrator 71 during use. It has been found for example, by providing a microwavable therapeutic pad 70 an increased therapeutic sensation is achieved for aching muscles and the like. As the liquid filled sponge 76 is agitated during use, the heated liquid therein and about is stirred and the warmth is evenly distributed to the sore muscles more uniformly. The process of using pad 70 in its microwavable form consists of removing it from vibrator 71, placing pad 70 in a microwave oven for a sufficient length of time for heating. Thereafter pad 70 is removed and placed on vibrator 71 for use. For cold therapy, pad 70 would be placed in a freezer or the like to prepare it for usage.

Figure 15:
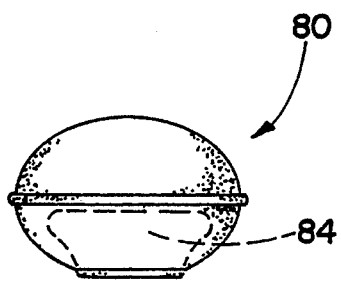
FIG. 15 illustrates the pad as shown in FIG. 14 from a side view.
Figure 14:
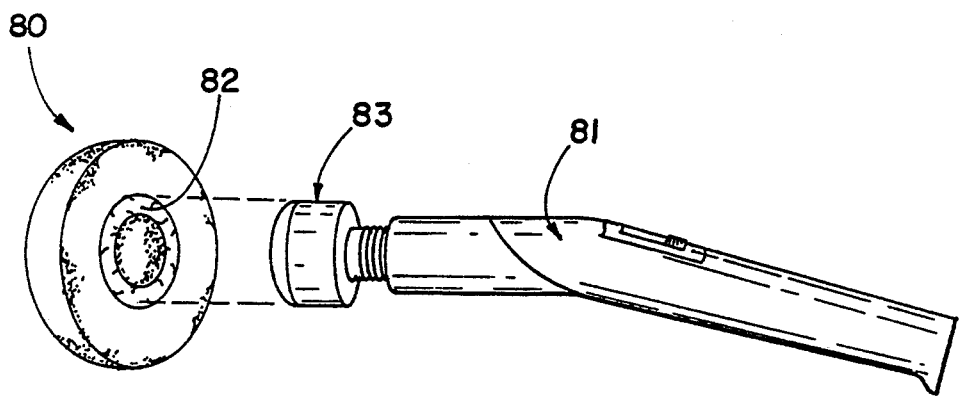
FIG. 14 shows yet another commercially available battery powered vibrator with a dome-like pad removed therefrom.

In FIGS. 14 and 15, another vibrator covering pad 80 is shown. Vibrator 81 is battery operated and like vibrator 71, is commercially available. Substantially dome-shaped therapeutic pad 80 has an elastic or resilient rim 82 which stretches to allow vibrator head 83 to enter cavity 84 therein. Dome-shaped therapeutic pad 80 is generally constructed, except for its outer appearance, as is cylindrical therapeutic pad 70 shown in FIGS. 12 and 13 and likewise can be either a hot or cold therapy type pad.

Figure 16:
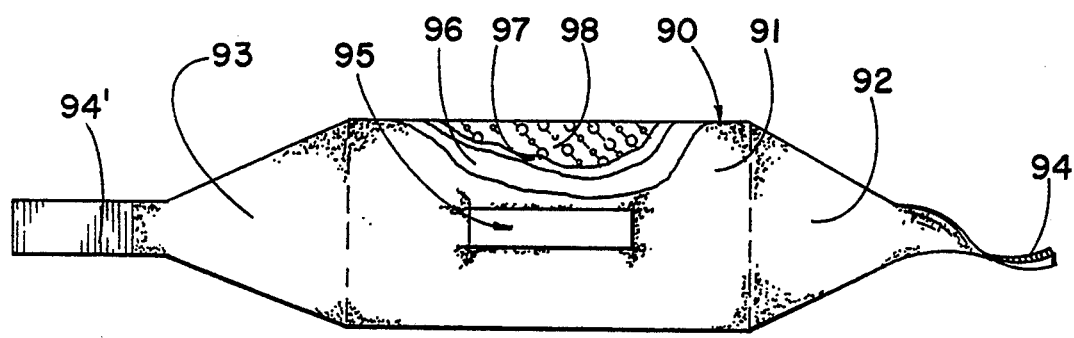
FIG. 16 shows a top plan view of a face or stress mask in partial cut-away form.
Figure 17:
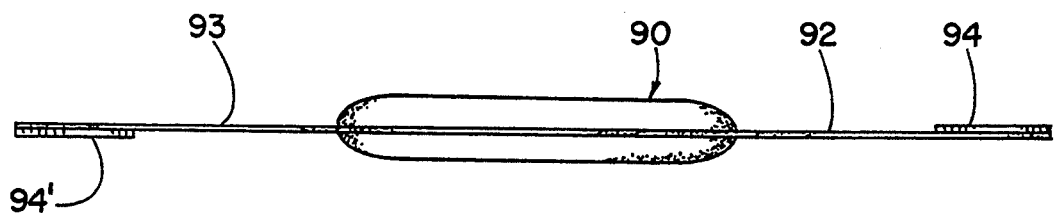
FIG. 17 illustrates a side elevational view of the mask as shown in FIG. 16.
Figure 18:
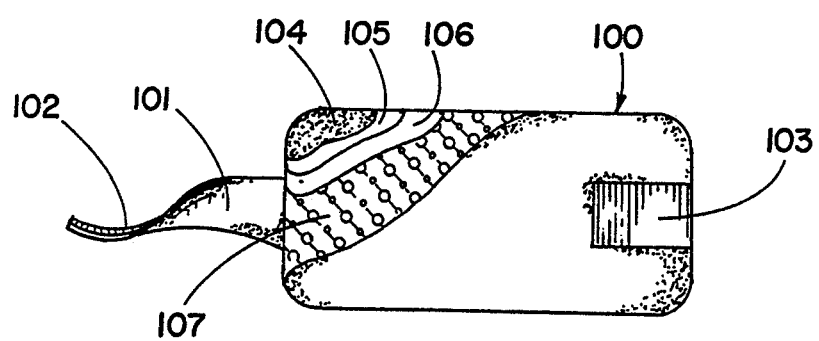
FIG. 18 shows a neck or arm pad having a cut-away section.

Another use of a hot or cold therapeutic pad is shown in FIGS. 16 and 17 whereby face mask 90 is presented. As shown, face or stress mask 90 consists of an outer cloth covering 91 with end flaps 92, 93 having hook and loop fasteners 94, 94' respectively affixed thereto. Mask 90 can be placed across the forehead and eye slot 95 allows the wearer to watch television or the like while mask 90 is worn. Mask 90 may be internally constructed similarly to therapeutic cylindrical pad 70 in FIG. 13 with a rubberized coating 96, a plastic envelope 97 and a liquid filled sponge 98 contained therein. FIG. 17 illustrates a side view of the device as shown in FIG. 16 illustrating the relative thinness of mask 90 which may be approximately one inch in thickness. Face mask 90 has been found to be useful in relieving headaches or facial aches or soreness which may develop proximate thereto. A similar construction without the eye slot 95 is seen in FIG. 18 having only one strap 101 attached to therapeutic liquid filled arm pad 100. Hook and loop fasteners 102 and 103 allow pad 100 to be attached around the neck, arm or leg of the person. Pad 100 includes an outer covering of fabric 104, an inner rubberized coating 105 and a liquid filled sponge 107. Cold (freezable) or heat (microwavable) models are available depending on whether desired hot or cold therapy.

It has been found that the use of a therapeutic pad of the invention can be beneficially used by those who suffer from cold or painful feet. One method of such a use is shown in FIGS. 19-22 whereby comfortable footwear 110 is shown which consists of a bedroom type shoe. Only the right shoe is shown but as understood a pair of such shoes would be provided. Footwear 110 consists of a soft, flexible upper portion 111 and a unitary rubber sole 112. For added comfort lambs wool 113 (real or imitation) is positioned along the inner walls within foot cavity 114. Other types of footwear could likewise be adapted for use such as leather styles.

Figure 19:
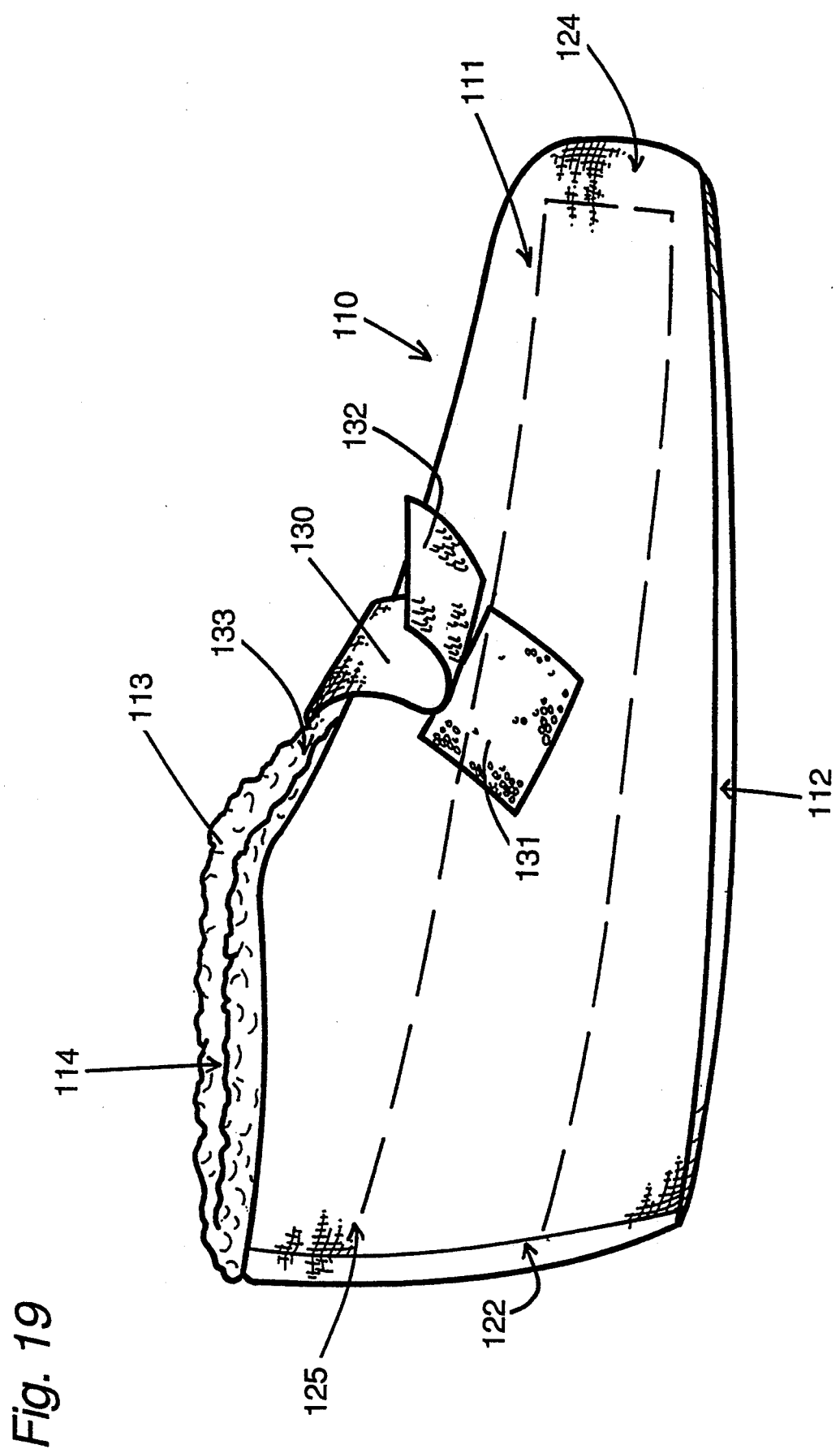
FIG. 19 depicts footwear which contains a therapeutic pad of the invention.
Figure 20:
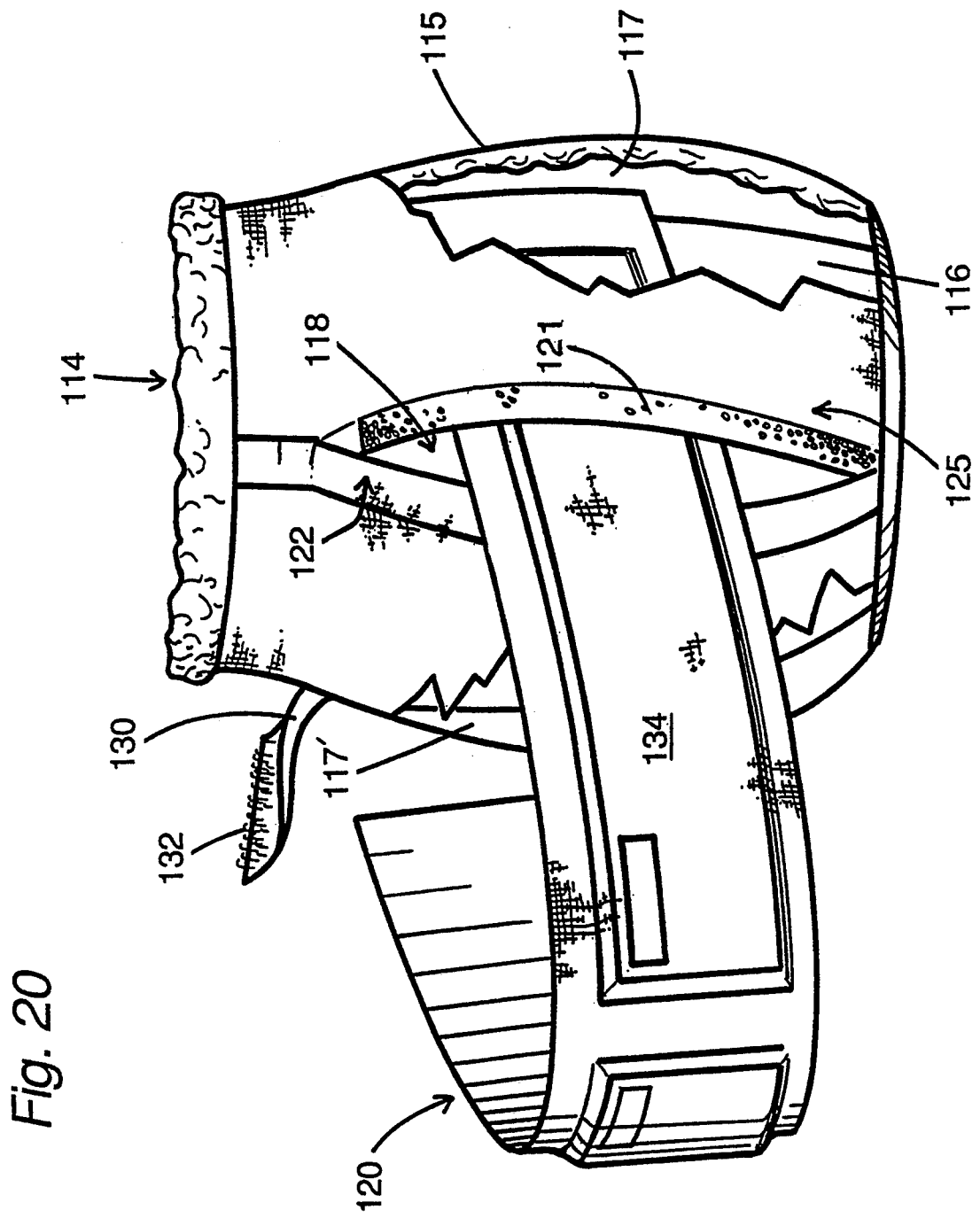
FIG. 20 pictures a rear view of the footwear as shown in FIG. 19 with a therapeutic pad partially inserted therein.

Upper portion 111 comprises a pair of walls 115, 116, as shown in FIG. 20 and includes a toe area 124 and a heel area 125 (FIG. 19). Outside wall 115 and inside wall 116 define compartments 117, 117' for containing therapeutic pad 120. As further shown in FIG. 20 pad 120 can easily be slid into compartments 117, 117' through opening 118 formed along the rear of upper portion 111. Opening 118 is defined by right side compartment opening 121 and left side compartment opening 122 as shown in FIG. 20. Hook and loop fastening material is placed on respectively, right side compartment opening 121 and left side compartment opening 122 to provide a means for securely closing compartment opening 118.

In order to provide a limited number of shoe or slipper sizes, foot cavity 114 is somewhat adjustable by strap 130 which may comprise a nylon material as does outside wall 115 as shown in FIG. 20. Adjusting strap 130 is adjustably attachable to strap catch 131. Strap catch 131 and terminal end 132 of adjusting strap 130 are formed from a hook and loop fastening material to cooperatively engage when positioned by the wearer. Adjusting strap 130 can be used to draw V-like opening 133 closed along the front of upper portion 111. As would be understood by those skilled in the art various other means could be employed to adjust the shoe to the wearer's foot such as conventional laces, stretchable elastic bands and the like.

Figure 21:
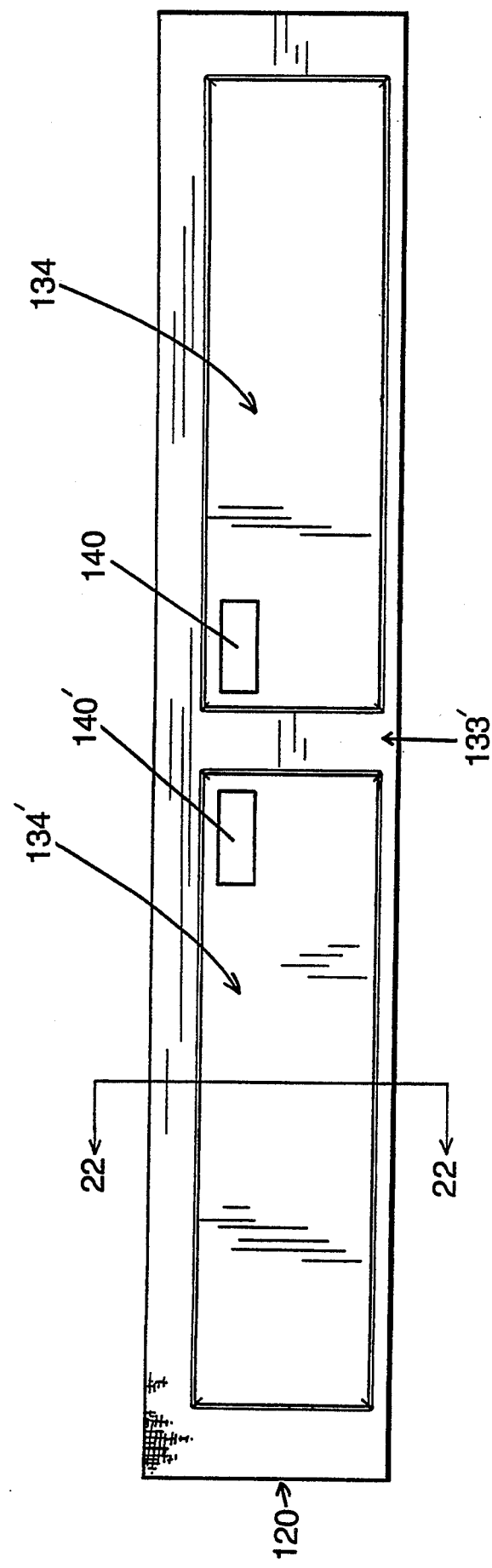
FIG. 21 demonstrates a therapeutic pad as used in FIG. 20.
Figure 22:
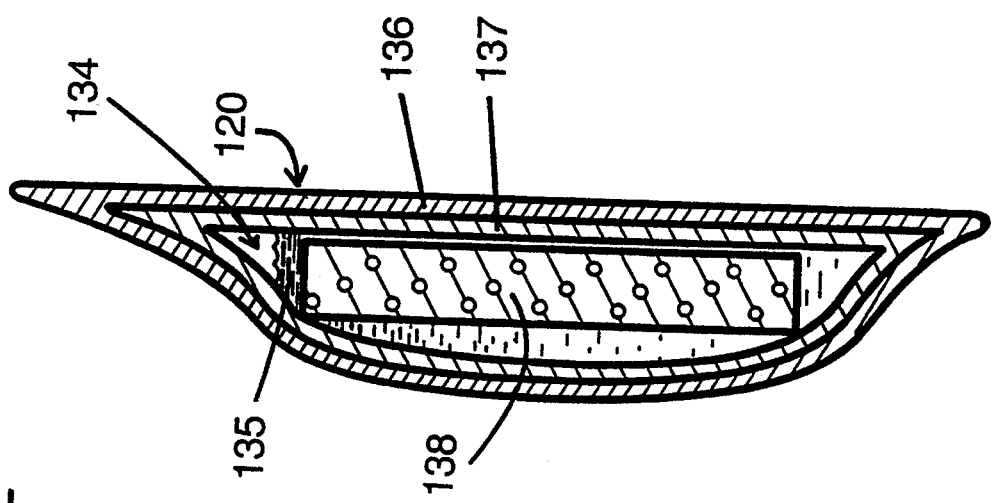
FIG. 22 illustrates a cross-sectional view of the pad along lines 22—22 of FIG. 21.

Therapeutic pad 120 is shown in relatively flat form in FIG. 21 and is approximately one-half inch thick and as illustrated provides thin, elongated vessels 134, 134' for holding a microwavable liquid 135 therein as shown in FIG. 22. Therapeutic pad 120 may be approximately twenty to twenty-four inches long, and two to three inches wide for an adult size slipper.

As further seen in FIG. 22, therapeutic pad 120 has an outer nylon covering 136 and inner pouch 137 which may be formed from a polymeric material to contain liquid 135 and absorbing means 138, which may be for example a nylon sponge. As seen in FIG. 21, therapeutic pad 120 comprises a pair of vessels 134, 134' with a divider section 133' therebetween. Divider section 133' allows for ease in folding therapeutic pad 120 as shown at FIG. 20 when inserting therapeutic pad into footwear 110.

Thermochromatic liquid crystal temperature indicators 140, 140' are shown on pad 120 in FIG. 21. The indicator will turn colors (for example, white to red) when sufficient heat has been applied by a microwave oven to pad 120. Temperature indicators 140, 140' are conventional and various types can be used to provide an indicator and safety device for the user.

In use, two therapeutic pads 120 are removed (from both left and right footwear) and are placed in a conventional microwave oven (not shown). Approximately five minutes of heating time at high setting is then allowed after which pads 120 are removed from the microwave oven and are inserted into the rear of footwear 110 as illustrated at FIG. 20. Rear opening 118 is then sealed by pressing left side compartment opening 122 over right side compartment opening 121. The wearer's foot can then be placed within cavity 114 and strap 130 positioned on strap catch 131 at the proper location therealong for the comfort of the wearer. Footwear 110 can then be worn for several hours by the user while heat is directed to the feet. Depending on the extent of therapeutic application desired by the user, therapeutic pad 120 can be removed and reheated as often as necessary to provide warmth and comfort to the feet of the wearer. Also, cold therapeutic pads as earlier discussed herein may be of benefit to certain footwear users.

As would be understood, footwear 110 and therapeutic pad 120 could be formed in a variety of configurations without departing from the scope of the invention and single or multiple vessels can be provided within therapeutic pad 120.

Another embodiment is shown in FIG. 23 whereby footwear 150 includes therapeutic pad 151. As further seen in FIG. 23, tongue 152 is attached inside toe area 153 of upper portion 166 such as by sewing or the like to form pad compartment 160 between top surface 155 of upper portion 166 and tongue 152 above foot cavity 170. Therapeutic pad 151 has a pointed or tapered end 156 as shown in FIG. 25 which allows it to be easily inserted between tongue 152 and top surface 155 of footwear 150 after heating.

As hereinbefore mentioned therapeutic pad 151 is suitable for heating in a microwave oven as it contains liquid absorbing means 158 which may be for example a nylon sponge. The outer covering of therapeutic pad 151 is formed from a nylon fabric and includes perimeter flange 157. Flange 157 may extend outwardly approximately one-quarter of an inch around the entire perimeter of therapeutic pad 151. Conventional temperature indicator 165 is affixed to the outer covering and turns red when the temperature reaches a desired level.

Therapeutic pad 151 may have a length "A" of five and one-half inches as seen in FIG. 25, a width "B" of four and one-half inches and a thickness of approximately five eighths of an inch. Therapeutic pad 151 is activated by placing it in a microwave oven for approximately one minute and thereafter, removing it from the microwave oven and sliding it into opening 160 between tongue 152 and top surface 155 of footwear 150 as shown in FIG. 24. As would be understood, only one half of a pair of footwear is shown and illustrated in FIGS. 23 and 24 but of course a pair would generally be used.

Upper portion 166 of footwear 150 may be a nylon fabric and includes lambs wool surface 167 (which may be real or imitation) and is joined to lightweight treaded sole 162. Various sizes and designs are available as desired.

Foot cavity 170 defines an upper foot entry aperture 171 which is surrounded by cuff 161 as seen in FIG. 24 which has lambs wool 167 outer surface. Tongue 152 has its under side likewise covered with lambs wool 167. Thus warmth and comfort can be provided for the wearer's feet as therapeutic pad 151 is reheated as desired although more than one hour of adequate heat is available after high wattage microwaving for only one minute.

The illustrations and examples provided herein are for explanatory purposes only and are not intended to limit the scope of the appended claims.

I claim:

1. Footwear with a therapeutic pad, comprising:
   (a) a sole;
   (b) an upper portion connected to said sole to form a foot cavity therebetween, said upper portion including a toe area;
   (c) a tongue joined to said upper portion in the toe area to form a therapeutic pad compartment between said tongue and said upper portion; and
   (d) a microwavable, liquid-filled therapeutic pad removably positioned within the therapeutic pad compartment above said tongue proximate the toe area and extending substantially throughout the toe area.

2. The footwear as defined in claim 1, wherein said therapeutic pad comprises:
   (a) a sealed flexible plastic envelope containing a liquid;
   (b) means for absorbing liquid compressed within said envelope; and
   (c) a water impervious covering around said envelope.

3. The footwear as defined in claim 1, wherein said upper portion includes a cuff.

4. The footwear as defined in claim 1, wherein said therapeutic pad has a tapered end.

5. The footwear as defined in claim 1, wherein said therapeutic pad has a temperature indicator.

6. The footwear as defined in claim 1, wherein said sole, said upper portion, and said tongue have a lambs wool outer surface.

7. Footwear with a therapeutic pad, comprising:
   (a) footwear having a therapeutic pad compartment;
   (b) a microwavable, liquid-filled therapeutic pad positioned within said compartment, said pad having:
      a sealed flexible plastic envelope containing a liquid,
      means for absorbing liquid compressed within said envelope, and
      a water impervious covering around said envelope;
   (c) a sole;
   (d) an upper portion connected to said sole to form a foot cavity therebetween, said upper portion including a toe area; and
   (e) a tongue joined to said upper portion in the toe area to form said therapeutic pad compartment between said tongue and said upper portion.

8. The footwear as defined in claim 7, wherein said liquid absorbing means comprises a sponge.

9. The footwear as defined in claim 7, wherein said upper portion includes a cuff.

10. The footwear as defined in claim 7, wherein said therapeutic pad has a tapered end.

11. The footwear as defined in claim 7, wherein said therapeutic pad has a temperature indicator.

12. The footwear as defined in claim 7, wherein said sole, said upper portion, and said tongue have a lambs wool-like outer surface.

* * * * *